(12) United States Patent
Winslow

(10) Patent No.: US 9,480,570 B2
(45) Date of Patent: Nov. 1, 2016

(54) POROUS METAL GLENOID AND ASSOCIATED METHOD FOR MOLDING THE SAME

(71) Applicant: Biomet Manufacturing, LLC., Warsaw, IN (US)

(72) Inventor: Nathan A Winslow, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 103 days.

(21) Appl. No.: 13/798,459

(22) Filed: Mar. 13, 2013

(65) Prior Publication Data

US 2014/0277517 A1 Sep. 18, 2014

(51) Int. Cl.
*A61F 2/40* (2006.01)
*B23K 15/00* (2006.01)
(Continued)

(52) U.S. Cl.
CPC ............... *A61F 2/4081* (2013.01); *A61L 27/04* (2013.01); *A61L 27/34* (2013.01); *A61L 27/56* (2013.01); *B23K 15/0006* (2013.01); *B29C 43/18* (2013.01); *B29C 70/68* (2013.01);
(Continued)

(58) Field of Classification Search
CPC ............... A61F 2/30; A61F 2/34; A61F 2/40; A61F 2/4081; A61F 2002/30028; A61F 2002/30029; A61F 2002/30004; A61F 2002/4085; A61F 2002/4088; A61F 2002/4092; A61F 2/30744; A61F 2/38; A61F 2/4003; A61F 2/42; A61F 2/4202; A61F 2/4225; A61F 2/4241; A61F 2/44; A61F 2/4612; A61F 2002/30736; A61F 2002/30744; A61F 2002/4003; A61F 2002/4007; A61F 2002/4011; A61F 2002/4081; A61F 2002/4096; A61F 2002/4205; A61F 2002/4207; A61F 2002/4212; A61F 2002/4217; A61F 2002/4226

USPC ................. 623/11.11, 18.11, 19.11
See application file for complete search history.

(56) References Cited

U.S. PATENT DOCUMENTS 5,164,187 A * 11/1992 Constantz et al. ............ 424/423
5,938,698 A * 8/1999 Sandoz ............... A61F 2/30724
623/16.11

(Continued)

FOREIGN PATENT DOCUMENTS

EP 1676548 A1 7/2006
EP 1676548 A1 7/2006

(Continued)

OTHER PUBLICATIONS

Abstract of WO2011138646 Nov. 2011 country WO, Pressacco M.*

(Continued)

*Primary Examiner* — Yashita Sharma
*Assistant Examiner* — Christie Bahena
(74) *Attorney, Agent, or Firm* — Schwegman Lundberg & Woessner, P.A.

(57) ABSTRACT

A porous metal glenoid component, comprising a thin solid nonporous region having a first side and a second side; a first porous metallic substrate formed on the first side of the nonporous region; a polymeric body fabricated onto the first porous metallic substrate, the polymeric body having an articulating surface configured to engage a humeral component to permit rotational and translational movement therewith; and a second porous metallic substrate formed on the second side of the nonporous region, the second porous metallic substrate being configured to interface with a glenoid cavity.

17 Claims, 6 Drawing Sheets

(51) Int. Cl.
  *B29C 43/18*   (2006.01)
  *B29C 70/68*   (2006.01)
  *A61L 27/04*   (2006.01)
  *A61L 27/34*   (2006.01)
  *A61L 27/56*   (2006.01)
  *A61F 2/30*    (2006.01)

(52) U.S. Cl.
  CPC ... *A61F 2/3094* (2013.01); *A61F 2002/30011* (2013.01); *A61F 2002/3092* (2013.01); *A61F 2002/30878* (2013.01); *A61F 2002/30971* (2013.01); *A61L 2430/24* (2013.01)

(56) References Cited

U.S. PATENT DOCUMENTS

| | | | |
|---|---|---|---|
| 7,208,222 B2* | 4/2007 | Rolfe | A61B 17/8605 428/131 |
| 2003/0014122 A1* | 1/2003 | Whiteside | A61F 2/389 623/20.32 |
| 2006/0069443 A1* | 3/2006 | Deffenbaugh et al. | 623/19.11 |
| 2009/0018560 A1* | 1/2009 | Mayer et al. | 606/151 |
| 2010/0331990 A1* | 12/2010 | Mroczkowski | A61F 2/4081 623/19.11 |
| 2011/0035013 A1 | 2/2011 | Winslow et al. | |

FOREIGN PATENT DOCUMENTS

| | | |
|---|---|---|
| EP | 1800700 A2 | 6/2007 |
| EP | 1800700 A2 | 6/2007 |
| WO | WO 2011/138646 A1 | 11/2011 |
| WO | WO-2014163958 A1 | 10/2014 |

OTHER PUBLICATIONS

International Search Report and Written Opinion for International PCT Application No. PCT/US2014/019297, May 14, 2014 (11 pages).
"Trabecular Metal Glenoid: The Natural Solution to Glenoid Fixation", Zimmer Brochure, (2009), 4 pages.
"Regenerex: Porous Titanium Construct", Biomet Brochure, (2008), 12 pages.
"International Application Serial No. PCT/US2014/019297, International Preliminary Report on Patentability mailed Sep. 24, 2015", 8 pgs.

* cited by examiner

POROUS METAL GLENOID AND ASSOCIATED METHOD FOR MOLDING THE SAME

TECHNICAL FIELD

The present teachings are generally related to a prosthetic device and associated methods for molding the same, and more particularly, to a porous metal glenoid component and associated methods for molding the same.

BACKGROUND OF THE DISCLOSURE

The statements in this section merely provide background information related to the present disclosure and should not be construed as constituting prior art.

Many portions of the human anatomy naturally articulate relative to one another. Generally, the articulation of these anatomic regions is smooth and non-abrasive in nature, particularly in the presence of natural tissues, such as cartilage and strong bone.

Over time, however, due to injury, stress, degenerative health problems and various other issues, the ease by which these anatomic regions are able to articulate degenerates in quality, thereby leaving the articulation of these anatomic regions abrasive and impractical. For example, injury may cause the cartilage or the bony structure to become weak, damaged, or even non-existent. As a result, the natural articulation of these anatomical regions is no longer possible for these affected individuals. At such times, it may be desirable to replace the affected anatomical regions with a prosthetic component so that normal articulation may be restored.

A humerus generally articulates within a glenoid surface or cavity in a shoulder. When implantation of a shoulder joint prosthesis becomes necessary, the natural head portion of the humerus can be resected and a cavity created in the intramedullary canal of the host humerus for accepting a humeral component. Moreover, the glenoid cavity positioned at the lateral edge of the scapula may also be resurfaced and shaped to accept the glenoid component. The humeral component includes a head portion used to replace the natural head of the humerus, while the glenoid component generally includes an articulating surface, which is engaged by the head portion of the humeral component.

Since glenoid components are subject to various types of loading by the head portion of the humeral component, the glenoid component must offer a stable and secure articulating surface. To achieve this, some glenoid components provide peripheral pegs which are inserted and cemented into holes bored into the glenoid cavity. Some of the pegged glenoid components utilize up to five peripheral pegs in order to stabilize and secure the glenoid component to the scapula.

While the peripheral pegs provide a means for securing the glenoid component to the glenoid cavity, it may also be desirable to ensure that at least a portion of the component is composed of a porous biocompatible material that is known to promote and facilitate the in-growth of surrounding bony and soft tissues. On the other hand, it may also be desirable to compose at least another portion of the component with a nonporous material. Because of technological limitations, however, manufacturing techniques have struggled to develop complex metal geometries having intermixed regions of porous and nonporous metals. The present application is intended to improve upon and resolve some of these known deficiencies of the art.

SUMMARY OF THE DISCLOSURE

In accordance with one aspect of the present application, a porous metal glenoid component is provided. In accordance with this aspect of the present disclosure, the glenoid component comprises a thin solid nonporous region having a first side and a second side; a first porous metallic substrate formed on the first side of the nonporous region; a polymeric body fabricated onto the first porous metallic substrate, the polymeric body having an articulating surface configured to engage a humeral component to permit rotational and translational movement therewith; and a second porous metallic substrate formed on the second side of the nonporous region, the second porous metallic substrate being configured to interface with a glenoid cavity.

According to another aspect of the present application, a glenoid component is provided and comprises a thin solid nonporous region having a first side and a second side; a first porous metallic substrate formed on the first side of the nonporous region; a polymeric body fabricated onto the first porous metallic substrate, the polymeric body having an articulating surface configured to engage a humeral component to permit rotational and translational movement therewith; and a second porous metallic substrate formed on the second side of the nonporous region, the second porous metallic substrate having at least one coupling stem configured to engage the glenoid cavity.

In accordance with still another aspect of the present application, a method for molding a porous glenoid component is provided. The method comprises the steps of: providing a glenoid component comprising a thin solid nonporous region having a first side and a second side; a first porous metallic substrate on the first side of the nonporous region; and a second porous metallic substrate on the second side of the nonporous region; placing the glenoid component into a molding tool so that the first porous metallic substrate is exposed to a molding chamber and the second porous metallic substrate is exposed to a non-molding chamber; and fabricating a polymeric body onto the first porous metallic substrate.

Still other objects and benefits of the application will become apparent from the following written description along with the accompanying figures.

BRIEF DESCRIPTION OF THE DRAWINGS

The above-mentioned aspects of the present application and the manner of obtaining them will become more apparent and the teachings of the present application itself will be better understood by reference to the following description of the embodiments of the present application taken in conjunction with the accompanying drawings, wherein.

Figure 1:
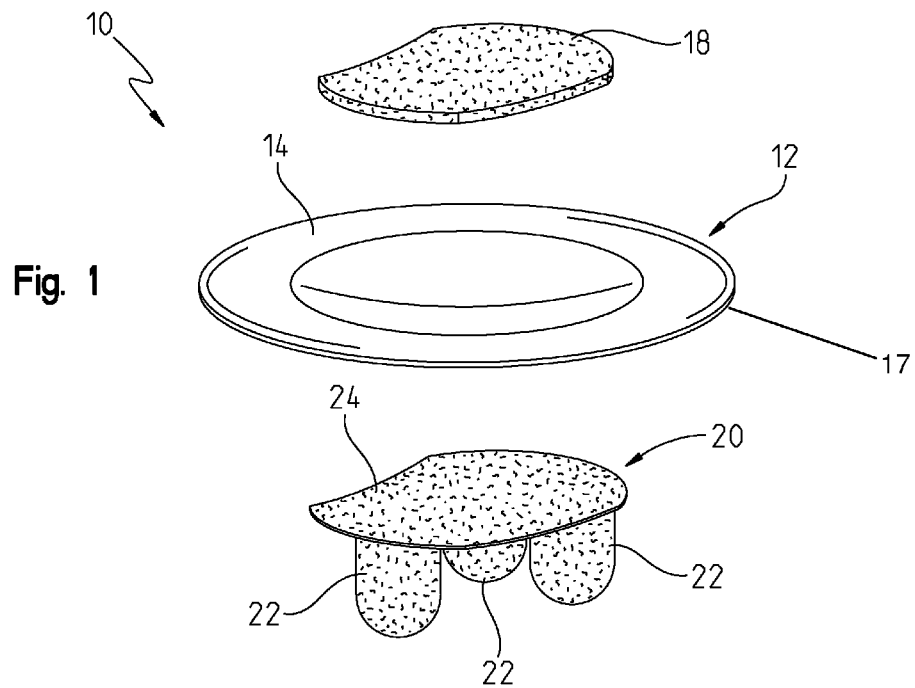
FIG. 1 represents an exploded perspective view of an illustrative porous metal glenoid component prior to injection molding or finish machining in accordance with the teachings of the present disclosure.

Corresponding reference characters indicate corresponding parts throughout the several views. Although the exemplification set out herein illustrates embodiments of the present application, in several forms, the embodiments disclosed below are not intended to be exhaustive or to be construed as limiting the scope of the present application to the precise forms disclosed.

DETAILED DESCRIPTION

The embodiments of the present application described below are not intended to be exhaustive or to limit the teachings of the present application to the precise forms disclosed in the following detailed description. Rather, the embodiments are chosen and described so that others skilled in the art may appreciate and understand the principles and practices of the present application.

Unless defined otherwise, all technical and scientific terms used herein have the same meaning as commonly understood by one of ordinary skill in the art to which this application belongs. Although any method and materials similar or equivalent to those described herein can be used in the practice or testing of the present application, the specific methods and materials are now described.

Figure 2:
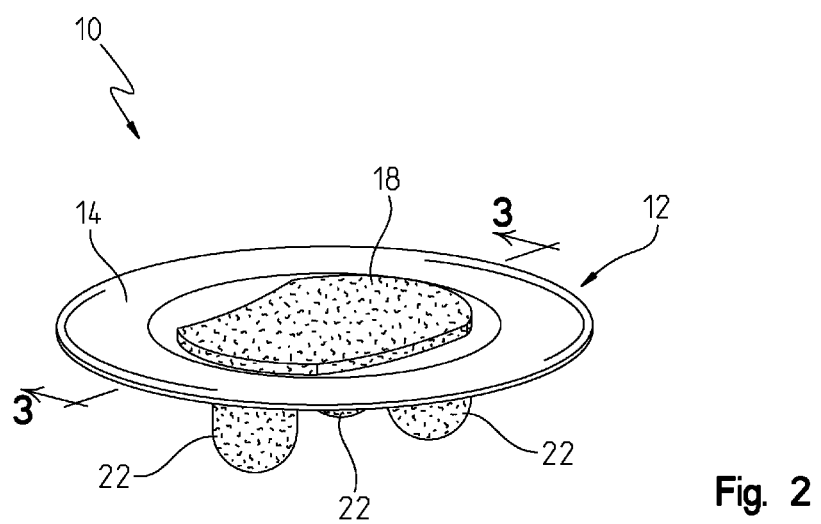
FIG. 2 represents a perspective view of the porous metal glenoid component of FIG. 1.
Figure 2A:
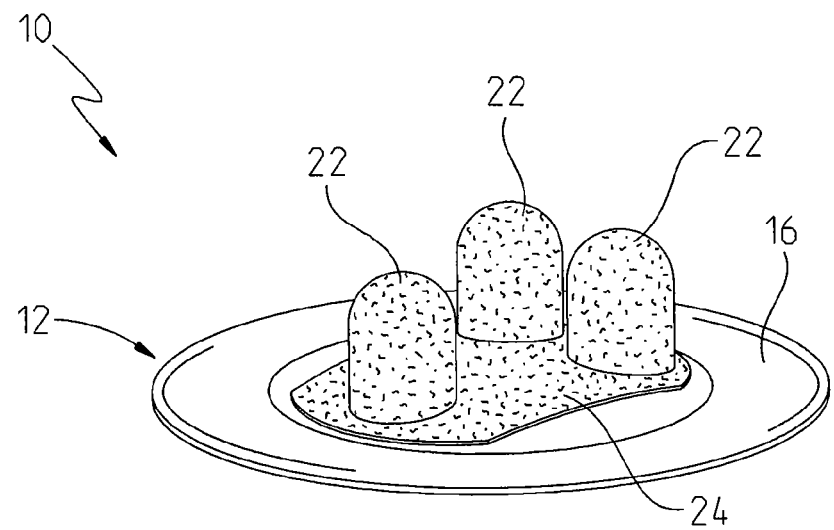
FIG. 2a represents another perspective view of the porous metal glenoid component of FIG. 1.
Figure 3:
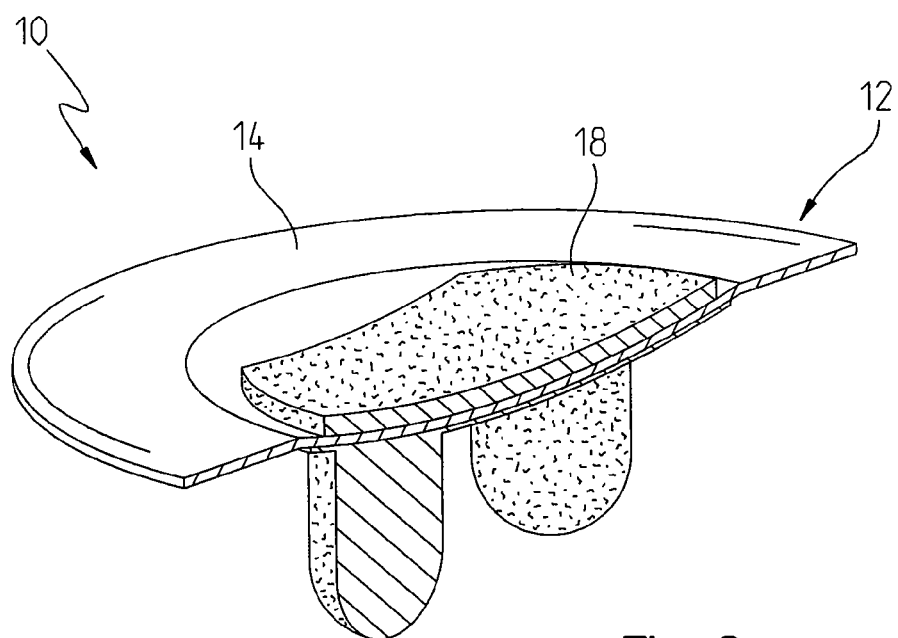
FIG. 3 represents a perspective cross-sectional view of the porous metal glenoid component of FIG. 1 and taken along the line 3-3 of FIG. 2.

Referring generally to FIGS. 1-3, an illustrative glenoid component 10 in accordance with the teachings of the present disclosure is provided. In accordance with this aspect of the present disclosure, the glenoid component 10 includes a thin solid (nonporous) region 12 having a first side 14 that is configured to function as a substrate onto which a polymeric material (e.g., polyethylene, also referred to as "poly") can be compression molded, and a second side 16 that is configured to interface with a glenoid cavity during a shoulder procedure (i.e., shoulder arthroplasty). The solid region 12 can be flat or curved to match the outer geometries of the glenoid component as desired (i.e., to match the articular curvature of the implantation face). The first side can have a concave center portion that can be surrounded by a first planar portion extending from the concave center portion to a first boundary (e.g., an edge) and the second side having a convex center portion surrounded by a second planar portion extending from the convex center portion to the first boundary.

To assist the first side 14 to function as a poly molding substrate, in accordance with certain aspects of the present teaching, at least a portion of the first side includes a porous metallic region or substrate pad 18. In accordance with this aspect of the present teachings, it has been determined that the porous nature of the metallic region 18 encourages poly to adhere better during compression molding so that long-term fixation of the poly to the substrate 18 can be achieved. Similarly, to assist the second side 16 to interface with the glenoid cavity during the implantation process, the second side also includes a porous metallic region or substrate pad 20. In accordance with this aspect of the present disclosure, the porous metallic region 20 includes one or more fixed peripheral peg coupling stems 22 that are configured to couple the glenoid component to a plurality of apertures defined within a resected glenoid cavity. Additionally, the porous metallic region 20 may also include a thin porous substrate or pad 24 surrounding the fixed peripheral peg coupling stems 22 to thereby increase the surface area available for bony in-growth or on-growth to occur once the device is implanted into the glenoid cavity.

In accordance with certain aspects of the present disclosure, the coupling stems 22 can be configured to include a first superior fixed peg and a pair of second inferior fixed pegs to form the corners of a triangle (e.g., an isosceles triangle). It should be understood and appreciated herein, however, that any desired configuration and/or number of coupling stems 22 can be used as desired without straying from the teachings of the present disclosure. As such, the present application is not intended to be limited herein.

The thin solid (nonporous) region 12 and the porous metallic regions 18, 20 may be formed from any suitable biocompatible metallic material, including, but not limited to, a titanium alloy (e.g., Ti-6Al-4V), CoCrMo and Pyrocarbon. In addition, the porous metallic regions 18 and 20 may be formed from a porous metallic construct (e.g., a porous titanium construct) or may be formed of a solid metallic construct having a porous region or layer applied thereon. Illustrative porous regions or layers that may be utilized to form the porous construct in accordance with the present disclosure include, but are not limited to, porous plasma sprays (PPS), Regenerex®, or Hydroxy Apatite (HA), or any other appropriate coating or region that promotes bony in-growth or on-growth. As those of skill in the art will understand and appreciate herein, providing the metallic regions 18, 20 with such a porous construct to promote bony in-growth or on-growth helps ensure that the glenoid component 10 is retained at a desired position within the resected glenoid once implanted.

Figure 4:
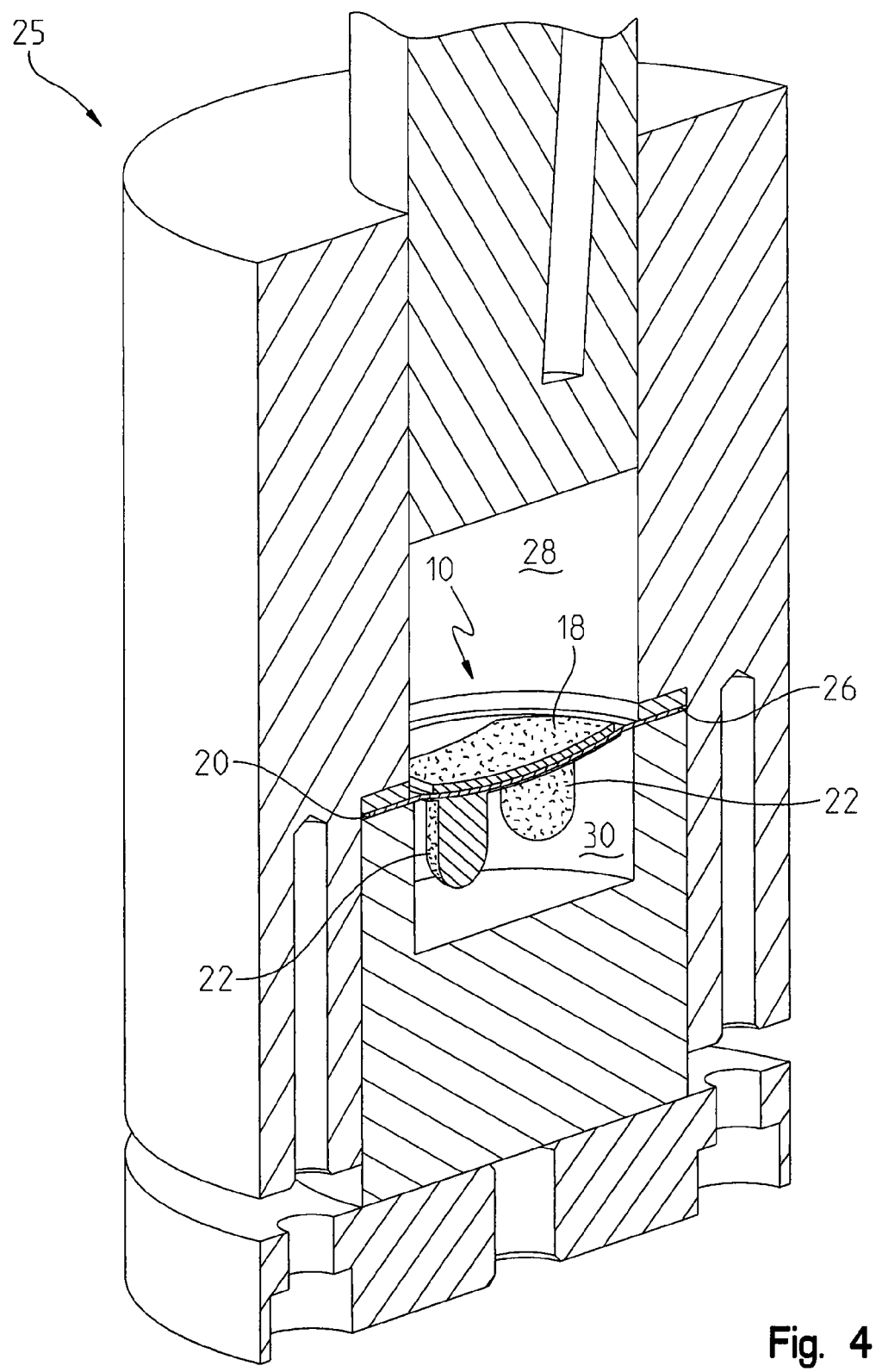
FIG. 4 represents a perspective cross-sectional view of an illustrative tool for compression molding a porous metal glenoid component in accordance with the teachings of the present disclosure.

Referring to FIG. 4, a cross-sectional view of an illustrative molding tool 25 for molding a polymeric glenoid body to the glenoid component 10 in accordance with the teachings of the present disclosure is provided. While it should be understood and appreciated herein that numerous different molding techniques and equipment can be used in accordance with the present disclosure without straying from the present teachings, according to one illustrative embodiment, the compression molding tool 25 has a horizontal slot 26 that separates the tool into upper and lower chambers 28, 30. The upper chamber 28 functions as a poly molding chamber such that when the glenoid component 10 is placed within the molding tool 25 (i.e., by inserting the solid nonporous region 12, which extends from the glenoid component into the horizontal slot 26), the solid region 12 functions as a barrier between the upper and lower chambers 28, 30 of the compression mold and provides a cantilevered portion to support the glenoid component in the molding tool. This barrier keeps the upper chamber 28 (i.e., the poly molding chamber) isolated from the bottom chamber 30, which houses the side of the glenoid component that will ultimately contact the bone. As this side of the glenoid component will directly contact bone, it should thereby be free and clear of poly, particularly so that the surrounding bone and tissue can grow into and around the porous construct without interference from the poly structure.

Figure 5:
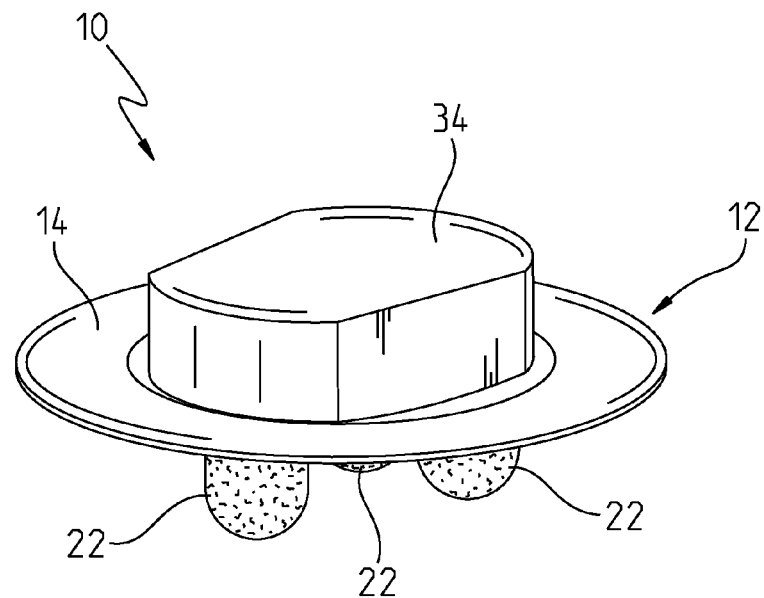
FIG. 5 represents a perspective view of an illustrative porous metal glenoid component after being molded in accordance with the teachings of the present disclosure.

Once the glenoid component 10 is inserted into the molding tool 25, polymer is dispensed (overmolded) onto the upper porous metallic region 18 and a glenoid body 34 formed (FIG. 5). The glenoid body 34, once molded includes an outer surface defining a boundary 35 which is displaced from the boundary 17. To form the glenoid body 34 in accordance with the teachings of the present disclosure, an overmolding process can be utilized in which the upper porous metallic region 18 is doped with polyethylene and then machine finished. Alternatively, the component can be profiled and then machined down (post molding) to match the profile.

Numerous different polymeric materials are known in the art for forming biomedical implant devices and can be used in accordance with the present disclosure. Such polymeric materials include, but are not limited to, sintered ultrahigh molecular weight polyethylene (UHMWPE) powders or mixture of powders. Such UHMWPE materials may be prepared almost entirely from UHMWPE powder, or may be formed by combining UHMWPE powder with other suitable polymer materials (e.g., GUR 1020 and GUR 1050 available from Ticona Engineering Polymers).

Figure 5A:
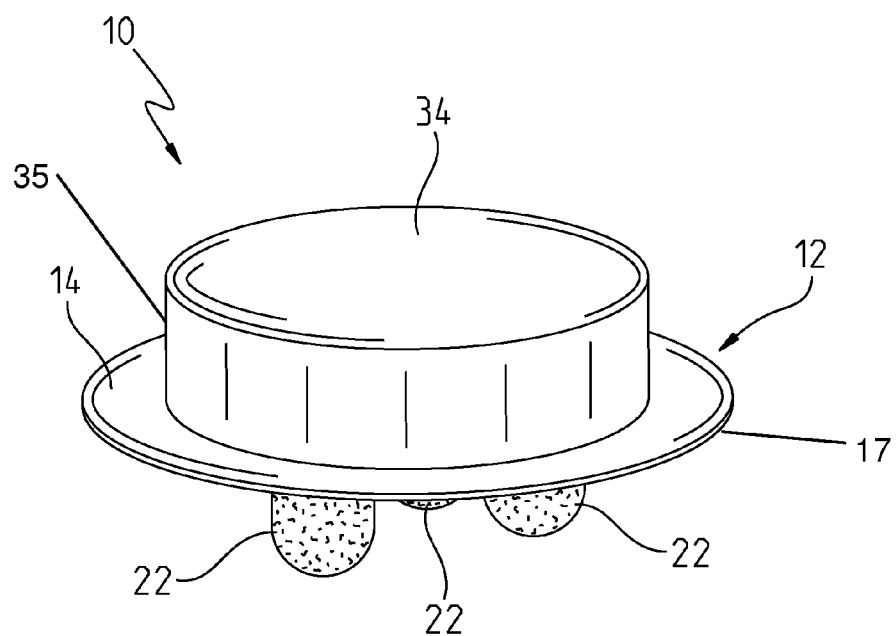
FIG. 5a represents a perspective view of another illustrative porous metal glenoid component after being molded in accordance with the teachings of the present disclosure.

While glenoid components may be formed from a traditional manufacturing method such as, for example, machining or forging, in accordance with certain aspects of the present disclosure, the glenoid component 10 may be formed from an additive manufacturing process such as Electron Beam Melting (EBM) or Direct Metal Laser Sintering (DMLS). As those of skill in the art will understand and appreciate herein, utilizing an additive manufacturing process allows the glenoid component 10 to be formed with or without an articular surface. Moreover, the final outer dimensions and articular surface can be machined to finish or molded to near net conditions (i.e., a condition that requires a small degree of further manipulation, such as polishing or smoothing, to produce the final surface). For example, FIG. 5 depicts a glenoid component after being molded (and prior to finish machining) where the outer geometry is near net, while FIG. 5a depicts a glenoid component after being molded where the outer geometry is particularly useful for E1 doping (i.e., the polymer can be doped with vitamin E and then homogenized).

Figure 6:
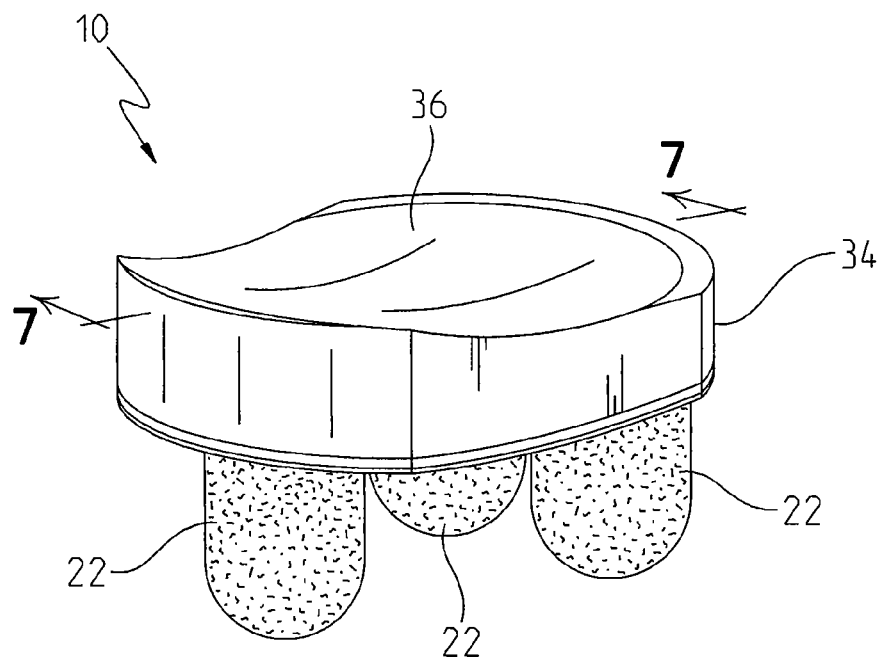
FIG. 6 represents a perspective view of an illustrative porous metal glenoid component after being machine finished in accordance with the teachings of the present disclosure.
Figure 6A:
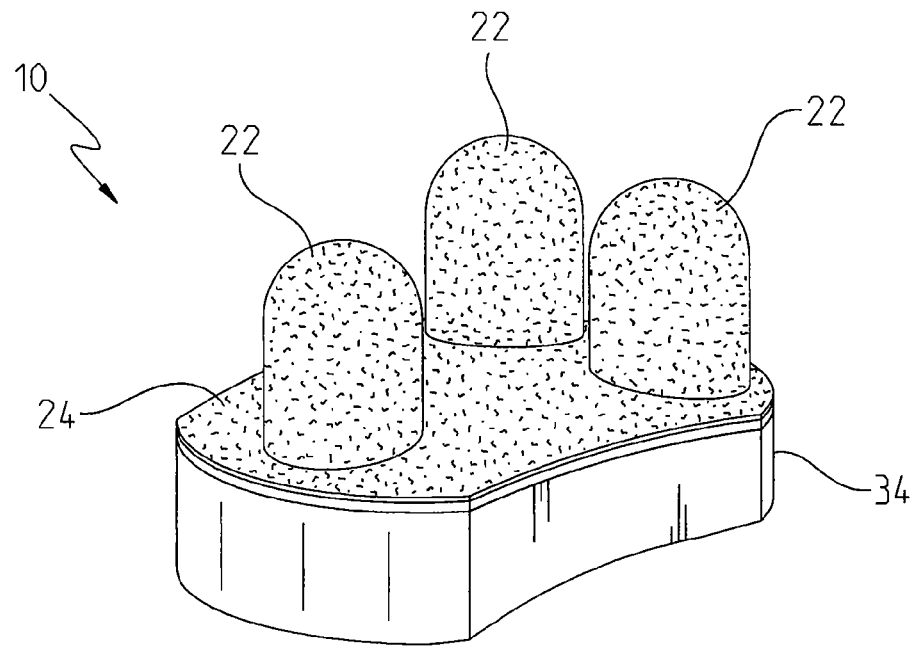
FIG. 6a represents another perspective view of the porous metal glenoid component of FIG. 6.
Figure 7:
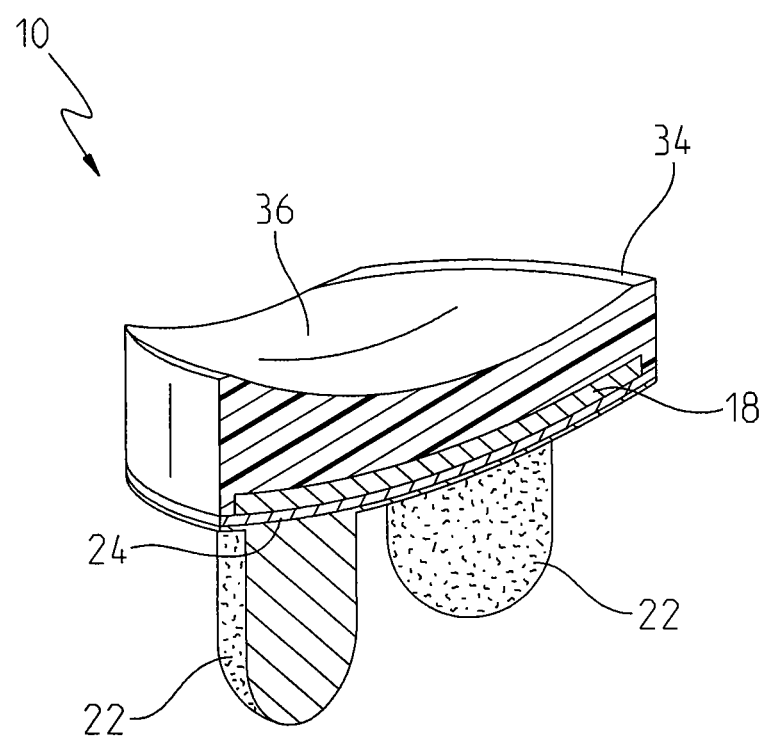
FIG. 7 represents a perspective cross-sectional view of the porous metal glenoid component of FIG. 6 and taken along the line 7-7 of FIG. 6.

After the glenoid body 34 is formed, it can then be machined into final form as desired and/or to match the anatomy of a specific patient as established in accordance with a surgeon-approved pre-operative plan. In particular, a generally spherical articulating surface 36 (FIG. 6) is formed into the top side of the glenoid body 34 to permit rotational and translational movement of the head of a humeral component or natural humerus against such surface 36. As illustrated, a portion of the solid region 12 has also been removed. As those of skill in the relevant art should understand and appreciate herein, various different processes for machine finishing the dimensional attributes of medical implant devices are known with the art, including, but not limited to, lathe and endmill processes. While all such machine finishing processes are intended to be incorporated into the teachings of the present disclosure, an illustrative example of a glenoid component 10 after undergoing a machine finishing process in accordance with the teachings of the present disclosure can be seen with reference to FIGS. 6-7.

While an exemplary embodiment incorporating the principles of the present application has been disclosed hereinabove, the present application is not limited to the disclosed embodiments. Instead, this application is intended to cover any variations, uses, or adaptations of the application using its general principles. Further, this application is intended to cover such departures from the present disclosure as come within known or customary practice in the art to which this present application pertains and which fall within the limits of the appended claims.

The terminology used herein is for the purpose of describing particular illustrative embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations).

What is claimed is:

1. A porous metal glenoid component, comprising:
a thin solid nonporous layer having a first side and a second side, wherein the first side and the second side terminate at edges thereof to define a first boundary, the first side having a concave center portion surrounded by a first planar portion extending from the concave center portion to the first boundary and the second side having a convex center portion surrounded by a second planar portion extending from the convex center portion to the first boundary;
a first metallic construct formed on the first side of the nonporous layer within the concave center portion, the first metallic construct being coated with a plasma spray, hydroxy apatite or a porous coating;
a polymeric body fabricated onto the first metallic construct, the polymeric body having an articulating surface configured to engage a humeral component to permit rotational and translational movement therewith and an outer surface extending from the articulating surface to the first metallic surface, the outer surface defining a second boundary, wherein the first boundary extends past the second boundary, the first planar portion and the second planar portion defining an extending portion of the thin solid nonporous layer which extends laterally beyond the polymeric body; and
a second metallic construct formed on the second side of the nonporous layer on the convex center portion, the second metallic construct being coated with a plasma spray, hydroxy apatite or a porous coating and configured to interface with a glenoid cavity, wherein the extending portion defines a support portion of the thin solid nonporous layer which extends laterally from the first metallic construct and the second metallic construct, the support portion having exposed first and second sides configured to be received by a molding tool.

2. The porous metal glenoid component of claim 1, wherein the thin solid nonporous layer is formed from a biocompatible metallic material.

3. The porous metal glenoid component of claim 1, wherein the first metallic construct comprises a porous region that encourages the polymeric body to adhere thereto when subjected to a compression molding process.

4. The porous metal glenoid component of claim 1, wherein the polymeric body is formed from polyethylene.

5. The porous metal glenoid component of claim 1, wherein the second metallic construct comprises a porous region that promotes bony in-growth or on-growth.

6. The porous metal glenoid component of claim 1, wherein the second metallic construct includes at least one coupling stem configured to engage the glenoid cavity.

7. The porous metal glenoid component of claim 1, wherein the concave portion of the thin solid nonporous layer is curved to match the articulating surface of the polymeric body.

8. The porous metal glenoid component of claim 1, wherein the support portion of the thin solid nonporous layer comprises a barrier configured to separate the first metallic construct formed on the first side of the nonporous layer from the second metallic construct formed on the second side of the nonporous layer such that the fabrication of the polymeric body fabricated onto the first metallic construct is isolated from the second metallic construct during fabrication.

9. The porous metal glenoid component of claim 1, wherein the exposed first side is substantially parallel to the exposed second side and the support portion extends continuously about the first metallic construct.

10. A glenoid component comprising:
a thin solid nonporous layer having a first side and a second side, wherein the first side and the second side define a first boundary at which each of the first side and the second side terminate, the first side having a concave center portion surrounded by a first planar portion extending from the concave center portion to the first boundary and the second side having a convex center portion surrounded by a second planar portion extending from the convex center portion to the first boundary, wherein the thin solid nonporous layer is circular;
a first metallic construct formed on the first side of the nonporous layer on the concave center portion, the first metallic construct being coated with a plasma spray, hydroxy apatite or a porous coating;
a polymeric body fabricated onto the first metallic construct, the polymeric body having an articulating surface defining a second boundary and configured to engage a humeral component to permit rotational and translational movement therewith, wherein the first boundary extends past the second boundary and along the articulating surface, the first planar portion and the second planar portion defining a circular extending portion of the thin solid nonporous layer which extends laterally beyond the polymeric body; and
a second metallic construct formed on the second side of the nonporous layer within the convex center portion, the second metallic construct being coated with a plasma spray, hydroxy apatite or a porous coating and having at least one coupling stem configured to engage the glenoid cavity, wherein the circular extending portion defines a support portion of the thin solid nonporous layer which extends laterally from the first metallic construct and the second metallic construct, the support portion having exposed first and second sides configured to be received by a molding tool.

11. The glenoid component of claim 10, wherein the thin solid nonporous layer is formed from a biocompatible metallic material.

12. The glenoid component of claim 10, wherein the first metallic construct comprises a porous region that encourages the polymeric body to adhere thereto when subjected to a compression molding process.

13. The glenoid component of claim 10, wherein the polymeric body is formed from polyethylene.

14. The glenoid component of claim 10, wherein the second metallic construct comprises a porous region that promotes bony in-growth or on-growth.

15. The glenoid component of claim 10, wherein the concave portion of the thin solid nonporous layer is curved to match the articulating surface of the polymeric body.

16. The glenoid component of claim 10, wherein the support portion of the thin solid nonporous layer comprises a barrier configured to separate the first metallic construct formed on the first side of the nonporous layer from the second metallic construct formed on the second side of the nonporous layer such that the fabrication of the polymeric body fabricated onto the first metallic construct is isolated from the coupling stem during fabrication.

17. The glenoid component of claim 10, wherein the exposed first side is substantially parallel to the exposed second side and the support portion extends continuously about the first metallic construct.

* * * * *